US008652195B2

United States Patent
Tani

(10) Patent No.: US 8,652,195 B2
(45) Date of Patent: Feb. 18, 2014

(54) ARTIFICIAL BLOOD VESSEL AND ARTIFICIAL BLOOD VESSEL SYSTEM

(75) Inventor: Kazuyoshi Tani, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 0 days.

(21) Appl. No.: 13/237,378

(22) Filed: Sep. 20, 2011

(65) Prior Publication Data

US 2012/0071960 A1  Mar. 22, 2012

(30) Foreign Application Priority Data

Sep. 21, 2010  (JP) .................................. 2010-210821
Jul. 7, 2011  (JP) .................................. 2011-150520

(51) Int. Cl.
*A61F 2/06* (2013.01)

(52) U.S. Cl.
USPC ........................ 623/1.13; 623/1.36; 623/23.64

(58) Field of Classification Search
USPC .............. 623/1, 13, 36, 1.1, 1.13, 1.36, 23.64
See application file for complete search history.

(56) References Cited

U.S. PATENT DOCUMENTS

| 6,773,457 | B2 * | 8/2004 | Ivancev et al. ................ 623/1.28 |
| 2002/0123790 | A1 * | 9/2002 | White et al. .................. 623/1.14 |
| 2002/0188344 | A1 * | 12/2002 | Bolea et al. .................. 623/1.11 |
| 2003/0176912 | A1 * | 9/2003 | Chuter et al. ................. 623/1.13 |
| 2005/0197690 | A1 * | 9/2005 | Molaei et al. ................. 623/1.13 |
| 2005/0288764 | A1 * | 12/2005 | Snow et al. ................... 623/1.11 |

* cited by examiner

*Primary Examiner* — David Isabella
*Assistant Examiner* — Randy Shay
(74) *Attorney, Agent, or Firm* — Buchanan Ingersoll & Rooney PC

(57) ABSTRACT

An artificial blood vessel includes a flexible tube and a structure provided at one end portion of the tube and capable of being deformed to a first outside diameter and a second outside diameter greater than the first outside diameter, wherein the tube is provided with a lock part which is locked at a desired position when the tube is folded back from its other end portion to the inside.

11 Claims, 12 Drawing Sheets

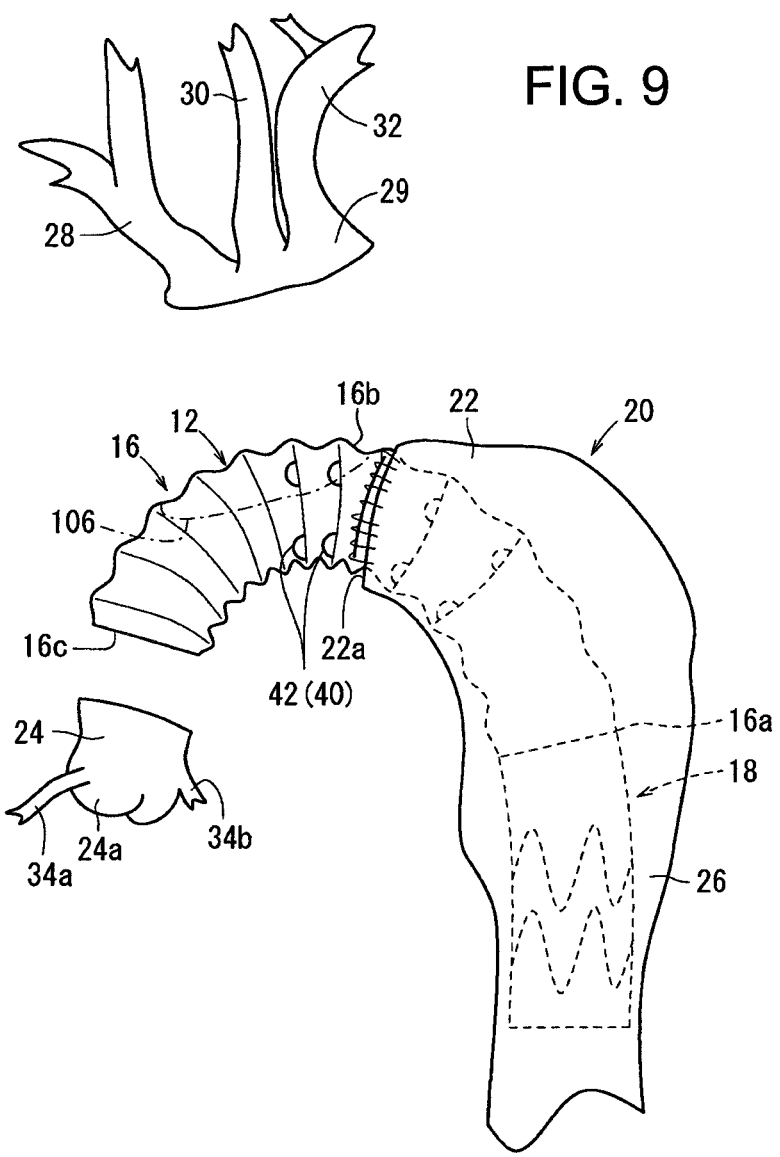

ARTIFICIAL BLOOD VESSEL AND ARTIFICIAL BLOOD VESSEL SYSTEM

This application claims priority under 35 U.S.C. §119 to Japanese Patent Application No. 2010-210821 filed on Sep. 21, 2010 and Japanese Patent Application No. 2011-150520 filed on Jul. 7, 2011, the entire content of both of which are incorporated herein by reference.

TECHNOLOGICAL FIELD

The present invention relates to an artificial blood vessel and an artificial blood vessel system for use in replacement surgery.

BACKGROUND DISCUSSION

Surgical therapy of aortic diseases (aortic aneurysm, aortic dissection, etc.) involves replacing the diseased aortic part with an artificial blood vessel. Especially, in the case of treatment of a wide range from the aortic arch to the descending aorta, an aortic arch replacement surgery is performed. This surgical operation uses an operative system (also called "frozen elephant trunk technique") wherein the aortic arch is trimmed, an artificial blood vessel provided with a stent at one end portion (an artificial blood vessel having a metallic skeleton for retaining a tubular form; also called "stent graft") is inserted into the living body blood vessel to reach the descending aorta, and the stent is pressed against the blood vessel wall. Thereafter an intermediate portion of the artificial blood vessel and the trimmed portion of the aortic arch (or descending aorta) are anastomosed with each other, and, further, the artificial blood vessel is anastomosed with other arteries. An example of this surgical operation is described in U.S. Pat. No. 6,773,457.

In the aortic arch replacement surgery, conventionally the anastomosis between the intermediate portion of the artificial blood vessel and the aortic arch includes a work in which, as shown in FIG. 4 of U.S. Pat. No. 6,773,457, the other end portion of the artificial blood vessel on the side where the stent is not provided (the artificial blood vessel section on this side is referred also to "tube" in contrast to the stent) is folded back to the inside (this work is also called "introversion"). This ensures that the folded end portion of the tube and the trimmed end portion of the aortic arch are anastomosed with each other comparatively easily and reliably. Consequently, the surgical operation time is shortened, and, further, the burden on the patient is alleviated.

The aortic arch replacement surgery normally involves only a thoracic midline incision to reduce the operative invasion exerted on the patient. As a result, the operative steps such as stent insertion, tube-artery anastomosis, etc. as mentioned above have to be carried out within a narrow operative region.

With such a narrow region, however, it is difficult to smoothly fold back the other end portion of the tube to the inside of the tube itself. Specifically, when attempts are made to fold back the tube to a desired position (folded end portion), a pushing-in force attendant on the folding-back work would cause the tube to be pushed into the aortic arch or the descending aorta, probably making it impossible for the tube to be folded back into the inside thereof in a desired shape. Consequently, the folding-back work becomes very troublesome, the working efficiency of replacement surgery is lowered, and the burden on the patient is increased considerably.

SUMMARY

The artificial blood vessel and artificial blood vessel system disclosed here is able to be locked at a desired position, whereby the tube can be easily folded back to the inside, so that a surgical operation for replacement with the artificial blood vessel can be carried out further efficiently, and the burden on the patient can be alleviated.

According to one aspect, an artificial blood vessel is configured to replace a portion of a blood vessel in a living body which has been removed from a remaining portion of the blood vessel in the living body. The artificial blood vessel comprises: a flexible tube having a portion configured to be fixed to a first part of the remaining portion of the blood vessel in the living body, with the flexible tube possessing an inside, one end portion and an oppositely located other end portion; and a structure fixed to the one end portion of the tube and configured to be positioned inside a second part of the remaining portion of the blood vessel in the living body, with the structure being deformable between a first outside diameter and a second outside diameter, with the second outside diameter being greater than the first outside diameter. The tube includes a lock part fixed to the tube and locked at a desired position when the tube is folded back from the other end portion to the inside of the tube.

The lock part provided on the tube of the artificial blood vessel is locked at a desired position when the work of folding back the other end portion of the tube to the inside is performed. Therefore, the tube can be prevented from being pushed into the living body blood vessel (for example, the aortic arch or the descending aorta) by a pushing-in force attendant on the folding-back work. Specifically, since the locking of the tube at a desired position helps ensure that the other end portion of the tube can be folded back to the desired position in a relatively short time, the surgery for replacement with the artificial blood vessel can be carried out more efficiently. The device for locking or fixing the lock part can be a position fixing device (described later), forceps and the like.

The tube is preferably provided at its outer peripheral surface with a plurality of the lock parts along an axial direction thereof. With the plurality of lock parts thus provided in the axial direction of the tube, it is possible to change the position of locking of the tube according to the region of therapy or the like and thereby to set the fold-back amount of the tube to the desired extent. This helps ensure that the folded end portion formed by folding back the tube can be assuredly positioned in the vicinity of a trimmed end portion of a living body blood vessel. Consequently, the anastomosis between the folded end portion and the trimmed end portion of the living body blood vessel can be further facilitated.

Further, preferably, the tube is bellows-like in shape and is provided with a plurality of the lock parts on a circling ridgeline at the outer peripheral surface of the tube. The plurality of lock parts thus provided on the ridgeline of the tube helps ensure that when the tube is folded back from the other end portion to the inside thereof, the plurality of lock parts are locked and, hence, the tube is held reliably. The positioned state of the tube is thus fixed even if a strong pushing-in force is exerted during the folding-back work.

The lock part may be an arcuate hooking part having both end portions fixed to an outer peripheral surface of the tube. With the arcuate hooking part thus used as the lock part, the arcuate hooking part can be easily attached to the outer peripheral surface of the tube. Where the lock part is thus composed of the arcuate hooking part, when the lock part is left at the outer peripheral surface of the artificial blood vessel it only projects to a relatively small extent as compared with an anastomosis thread upon anastomosis between the artificial blood vessel and the living body blood vessel, so that the lock part does not adversely affect the human body after the surgical operation.

According to another aspect, an artificial blood vessel system includes: an artificial blood vessel including a flexible tube and a structure provided at one end portion of the tube and capable of being deformed to a first outside diameter and a second outside diameter greater than the first outside diameter; and a position fixing device for positioning and holding the tube at a desired position when the tube is folded back from its other end portion to the inside.

This configuration helps ensure that at the time of folding back the other end portion of the tube to the inside in a surgical procedure for replacement with the artificial blood vessel, the tube can be positioned and held at a desired position using the position fixing device. With the tube thus positioned and held, the other end portion of the tube can be relatively easily folded back up to the desired position.

As a specific configuration for locking the tube, a configuration can be adopted in which the tube is provided with a lock part at an outer peripheral surface thereof, and the position fixing device has a hook section capable of engagement with the lock part. With the hook section possessed by the position fixing device and the lock part of the tube thus engaged with each other, the tube can be relatively easily positioned and held at a desired position.

In addition, the tube is preferably provided at its outer peripheral surface with a plurality of the lock parts along an axial direction thereof, and the hook section positions and holds the tube, in such a manner that the position of the tube in its axial direction can be changed, when the tube is folded back from its other end portion to the inside. With the plurality of the lock parts provided along the axial direction, the position at which the position fixing device positions and holds the tube can be changed selectively. This helps enable the fold-back amount of the tube to be arbitrarily set according to the size of the living body blood vessel (for example, the aortic arch or the descending aorta) to be replaced, the region of therapy, or the like.

The tube can be bellows-shaped and provided with a plurality of the lock parts on a circling ridgeline formed at an outer peripheral surface of the tube, and the position fixing device can have a plurality of hook sections corresponding to the lock parts to lock or fix the lock parts or the tube by virtue of engagement with the hook sections. The configuration in which the hook sections of the position fixing device lock the lock parts provided on the ridgeline of the tube helps ensure that the tube can be positioned and held reliably even if a strong pushing-in force is exerted thereon at the time of folding back the other end portion of the tube to the inside.

The position fixing device may be so configured as to pull the lock parts toward an outside diameter side in a state in which the lock parts are locked by the hook sections. With the lock parts thus pulled toward the outside diameter side by the position fixing device, the tube can be enlarged in inside diameter. Therefore, the work of folding back the tube from the other end portion to the inside can be carried out fairly easily, and, further, the folded end portion can be formed in a desired shape. This facilitates the anastomosis between the folded end portion of the tube and the trimmed end portion of the living body blood vessel, and enables the surgery for replacement with the artificial blood vessel to be carried out more efficiently.

Here, a configuration may be adopted in which the lock part is an arcuate hooking part having both end portions fixed to an outer peripheral surface of the tube, and the hook section projects to the inside of a U-shaped section which is opened on one side correspondingly to the arcuate hooking part and which accepts the tube. With the lock part thus being an arcuate hooking part and with the hook section thus projecting to the inside of the U-shaped section, it is relatively easy for the hook section to hook the arcuate hooking part, and, therefore, the tube can be rather easily positioned and held at a desired position.

In joining the artificial blood vessel by use of the artificial blood vessel system as above-described, the following method can be adopted.

The method of joining an artificial blood vessel to a living body blood vessel involves use of an artificial blood vessel comprising a flexible tube, a structure at one end portion of the tube and deformable to a first outside diameter and a second outside diameter greater than the first outside diameter, and a lock part configured to lock the tube at a desired position, the tube possessing an other end portion opposite the one end portion. The method involves: trimming the living body blood vessel and removing at least a portion of the living body blood vessel that is to be replaced with the artificial blood vessel; inserting the artificial blood vessel into the living body blood vessel to which the artificial blood vessel is to be joined to position the structure, possessing the first outside diameter, at an indwelling position in the living body blood vessel; expanding the structure from the first outside diameter to the second outside diameter while the structure is at the indwelling position; engaging a part of a position fixing device with the lock part of the tube to lock the tube; folding back the tube from the other end portion to the inside so as to form a folded end portion; and anastomosing the folded end portion of the tube with a trimmed end portion of the living body blood vessel.

When the tube is folded back from its other end portion to the inside during a surgery for replacement with an artificial blood vessel, the tube is locked at a desired position, whereby the other end portion of the tube can be rather easily folded back to the inside. This is effective in that the surgery for replacement with the artificial blood vessel can be performed more efficiently and that the burden on the patient can be lightened.

BRIEF DESCRIPTION OF THE DRAWING FIGURES

FIGS. 3A to 3C are schematic illustrations of the relationship between the artificial blood vessel and a position fixing device, wherein FIG. 3A is a side view of the artificial blood vessel, FIG. 3B is a side view showing a tube of the artificial blood vessel locked by the position fixing device, and FIG. 3C is a side view showing the other end portion of the tube is folded back to the inside;

Figure 4:
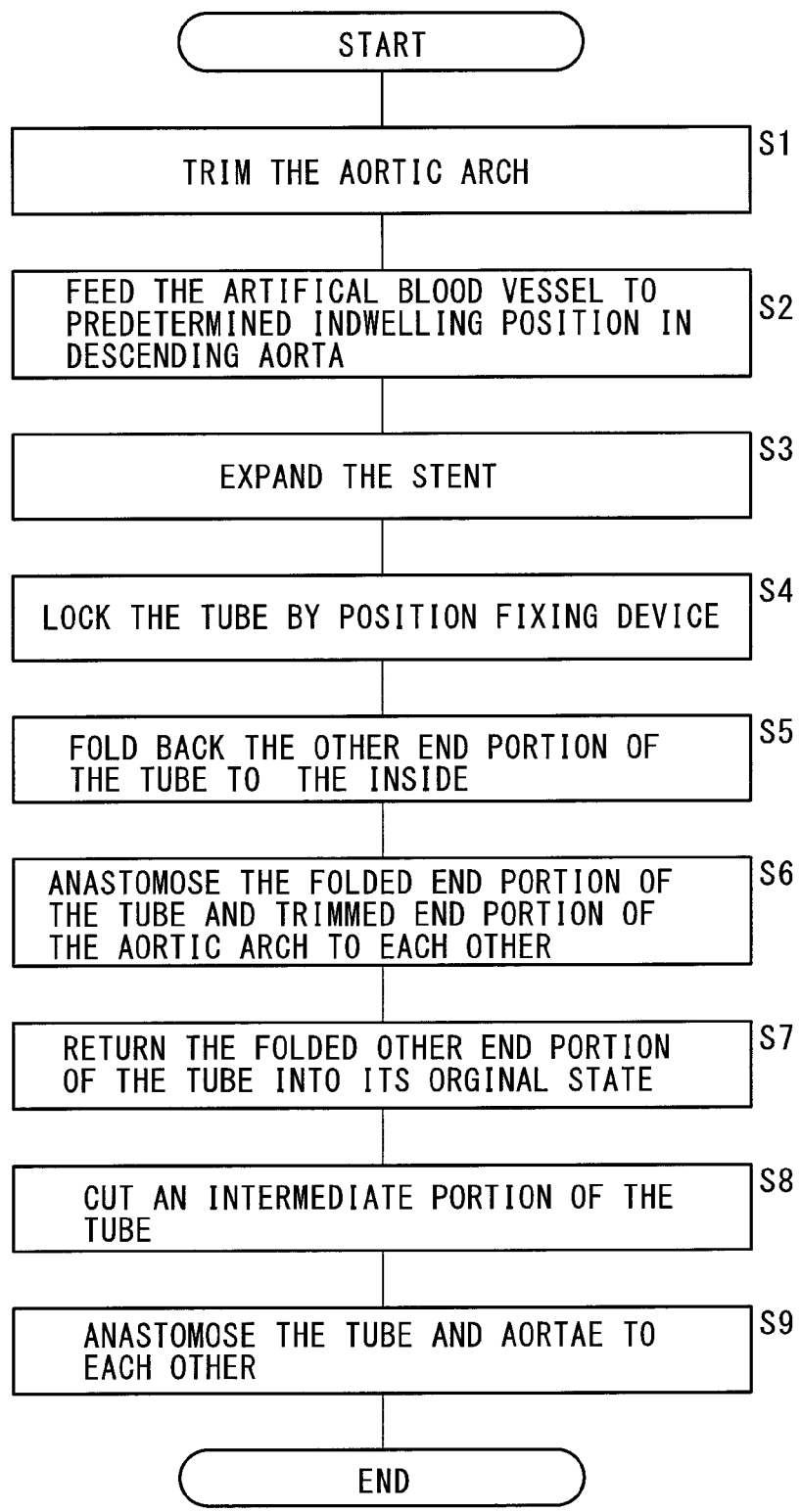

FIG. 4 schematically illustrates the procedure for performing an aortic arch replacement surgery using the artificial blood vessel system disclosed here.

Figure 5:
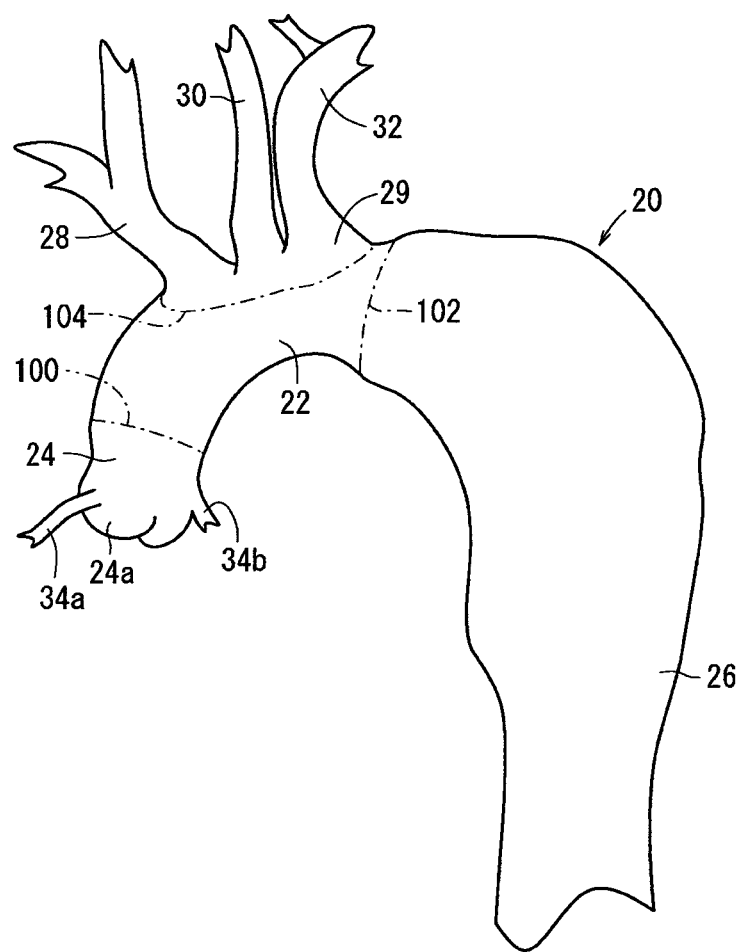

FIG. 5 is a schematic illustration of the vicinity of an aortic arch before being replaced with the artificial blood vessel.

Figure 6:
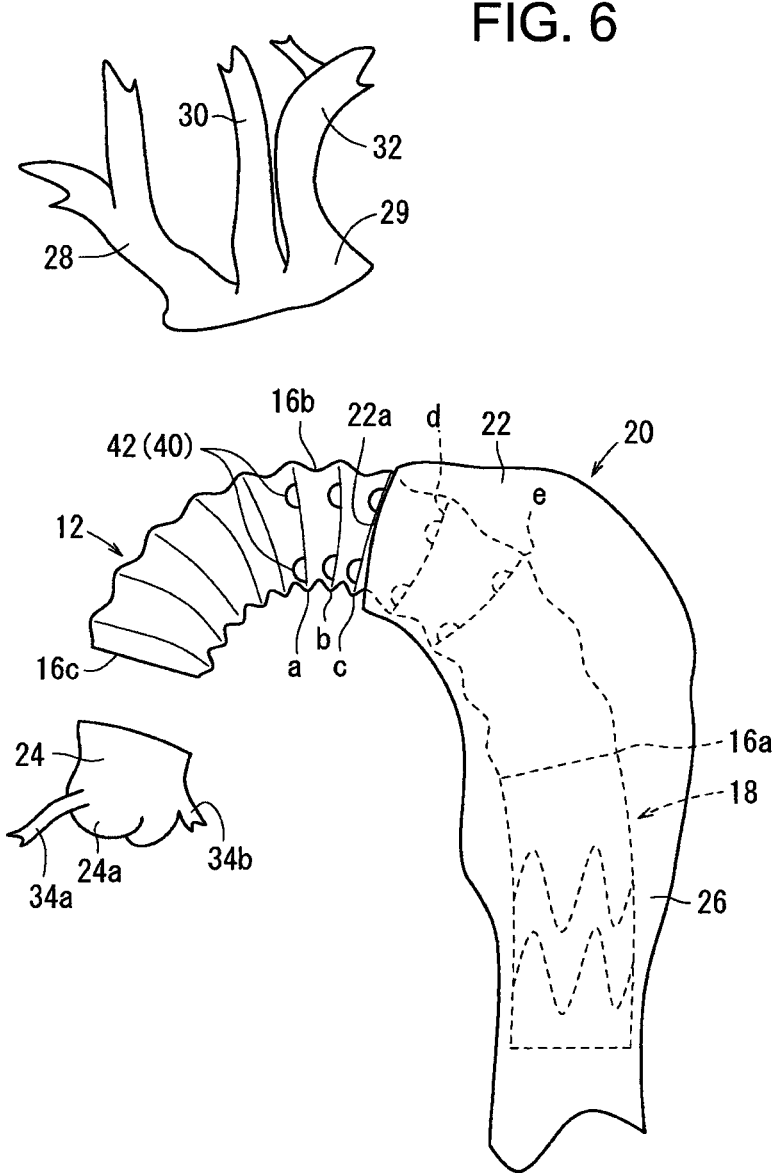
Figure 7:
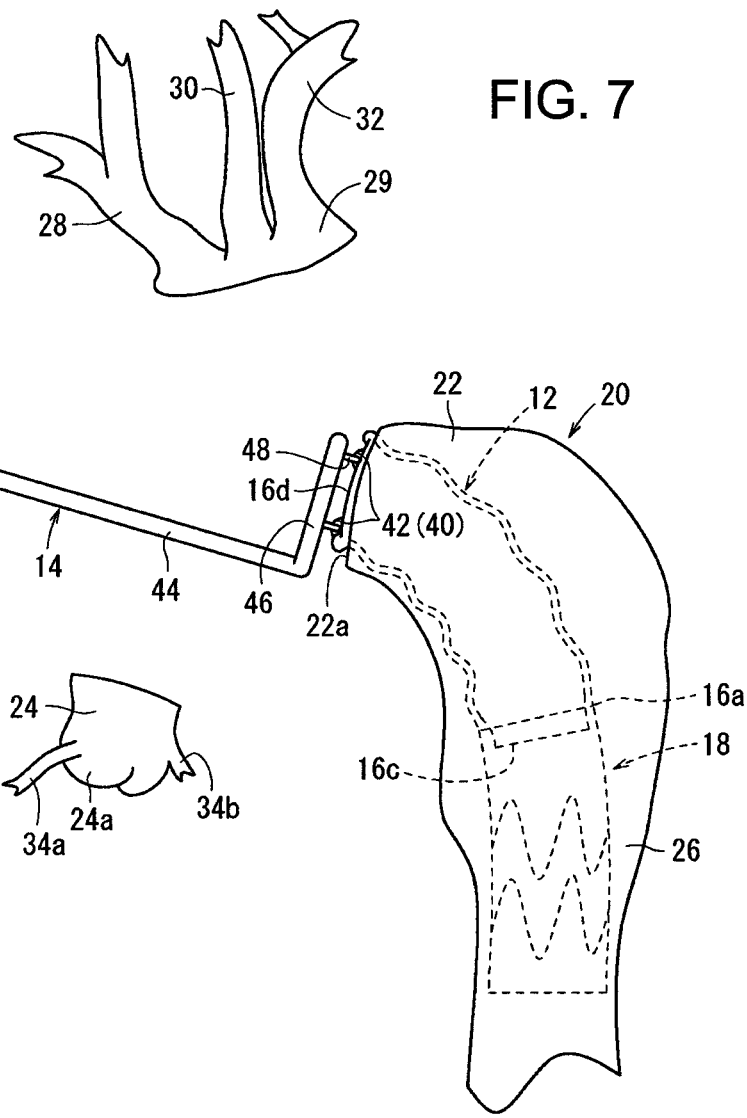

FIG. 6 is a schematic illustration of the artificial blood vessel inserted in a descending aorta;

FIG. 7 is a schematic illustration of the other end portion of the artificial blood vessel folded back.

Figure 8:
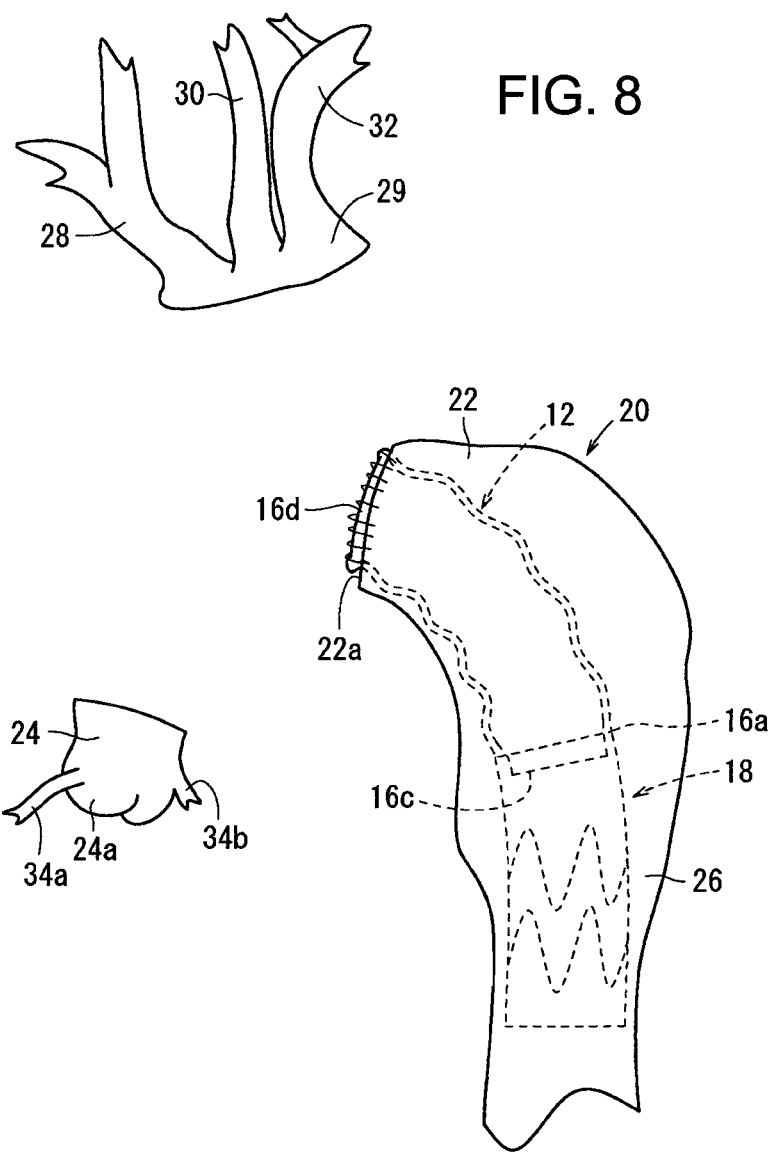

FIG. 8 is a schematic illustration of an intermediate portion of the artificial blood vessel and the descending aorta anastomosed with each other.

FIG. 9 is a schematic illustration of the other end portion of the artificial blood vessel returned to its original state.

Figure 10B:
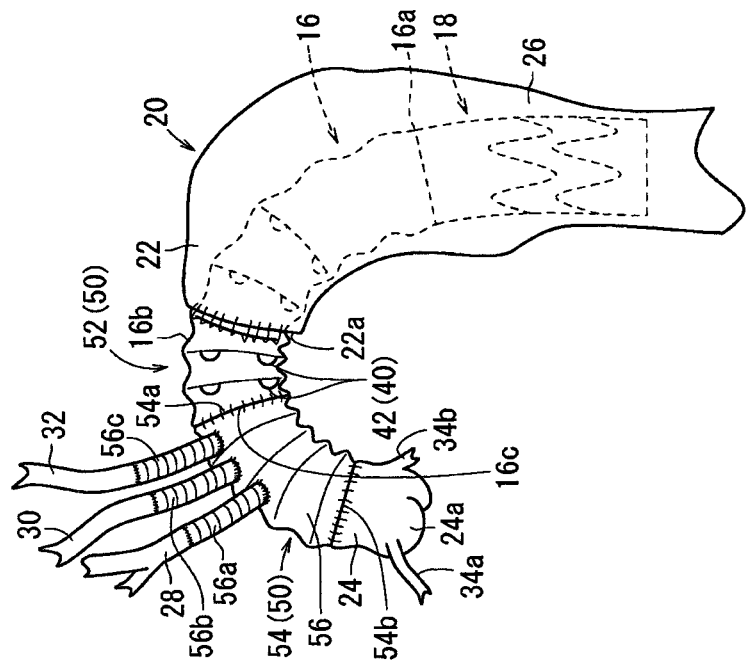
Figure 10A:
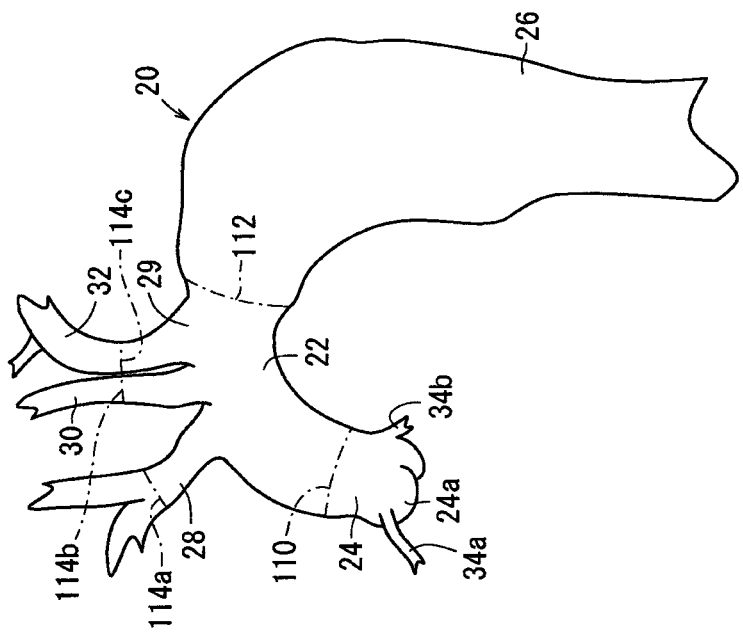

FIGS. 10A and 10B are illustrations of an artificial blood vessel according to a first modification, wherein FIG. 10A illustrates a trimmed portion of the aortic arch, and FIG. 10B illustrates an applied state of the artificial blood vessel according to the first modification.

Figure 11A:
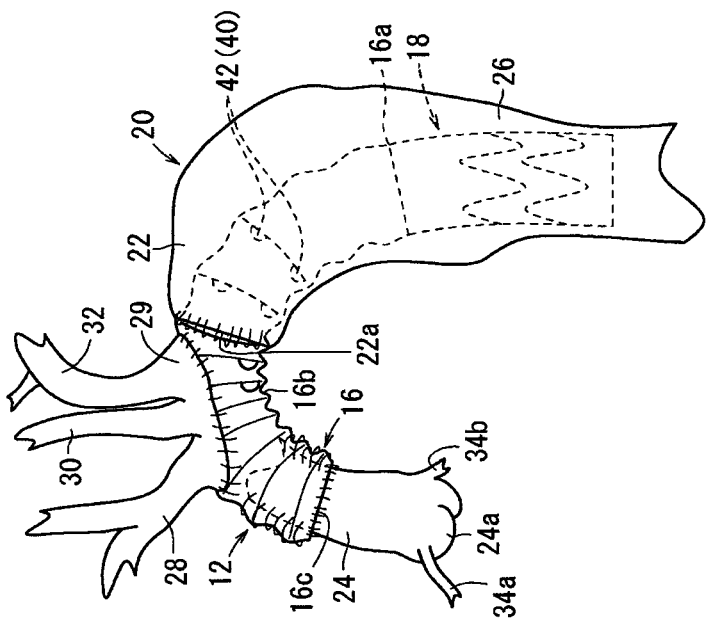
Figure 11B:
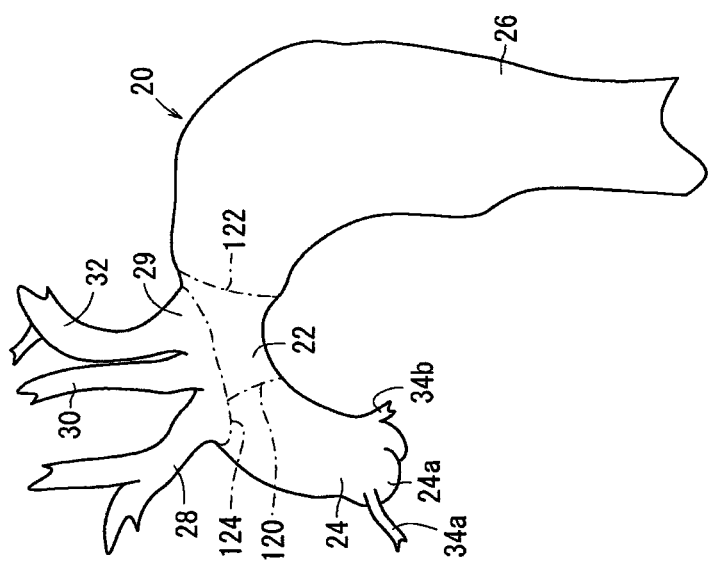

FIGS. 11A and 11B are illustrations of a method of joining the artificial blood vessel according to a second modification, wherein FIG. 11A shows a trimmed portion of the aortic arch, and FIG. 11B shows an applied state of the artificial blood vessel according to the second modification.

Figure 12A:
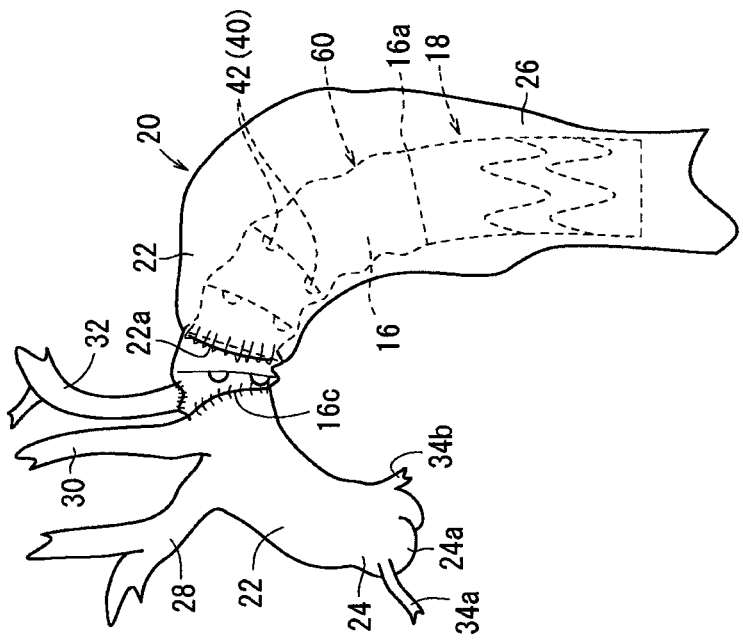
Figure 12B:
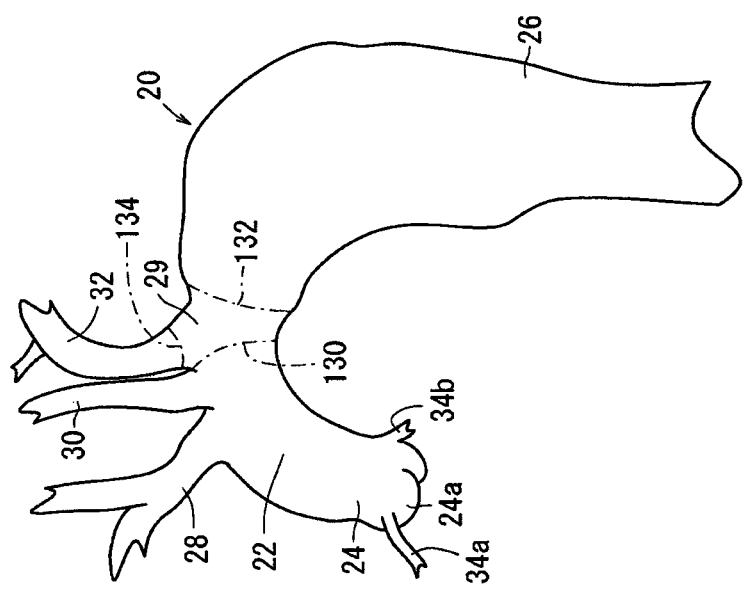

FIGS. 12A and 12B are illustrations of a method of joining an artificial blood vessel according to a third modification, wherein FIG. 12A shows a trimmed portion of the aortic arch, and FIG. 12B shows an applied state of the artificial blood vessel according to the third modification.

DETAILED DESCRIPTION

Figure 1:
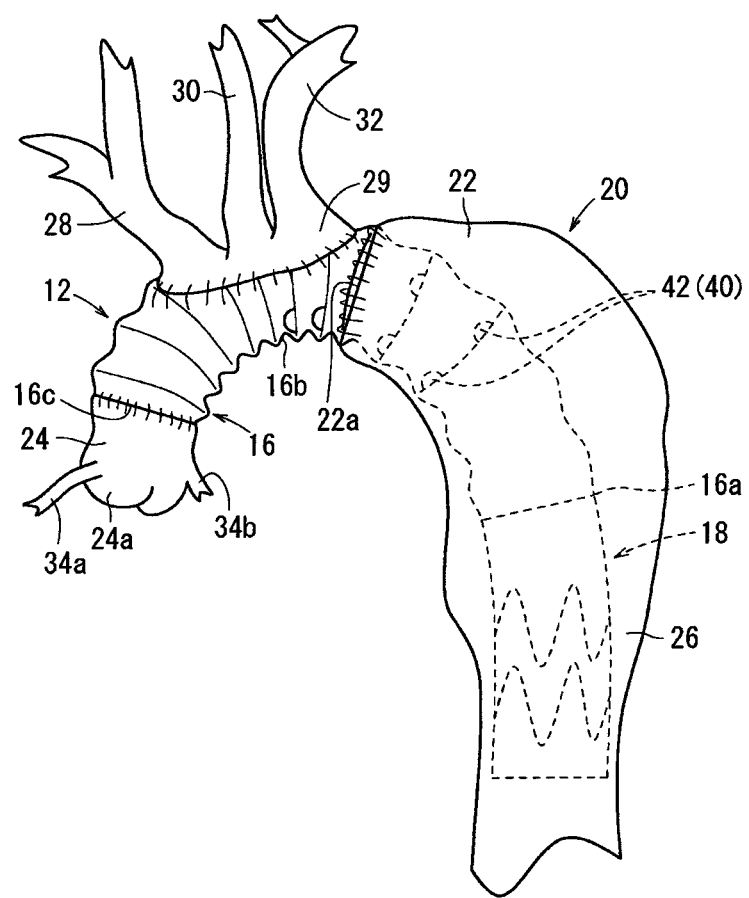
FIG. 1 is a schematic illustration of an artificial blood vessel according to an embodiment disclosed here applied to a living body.
Figure 2:
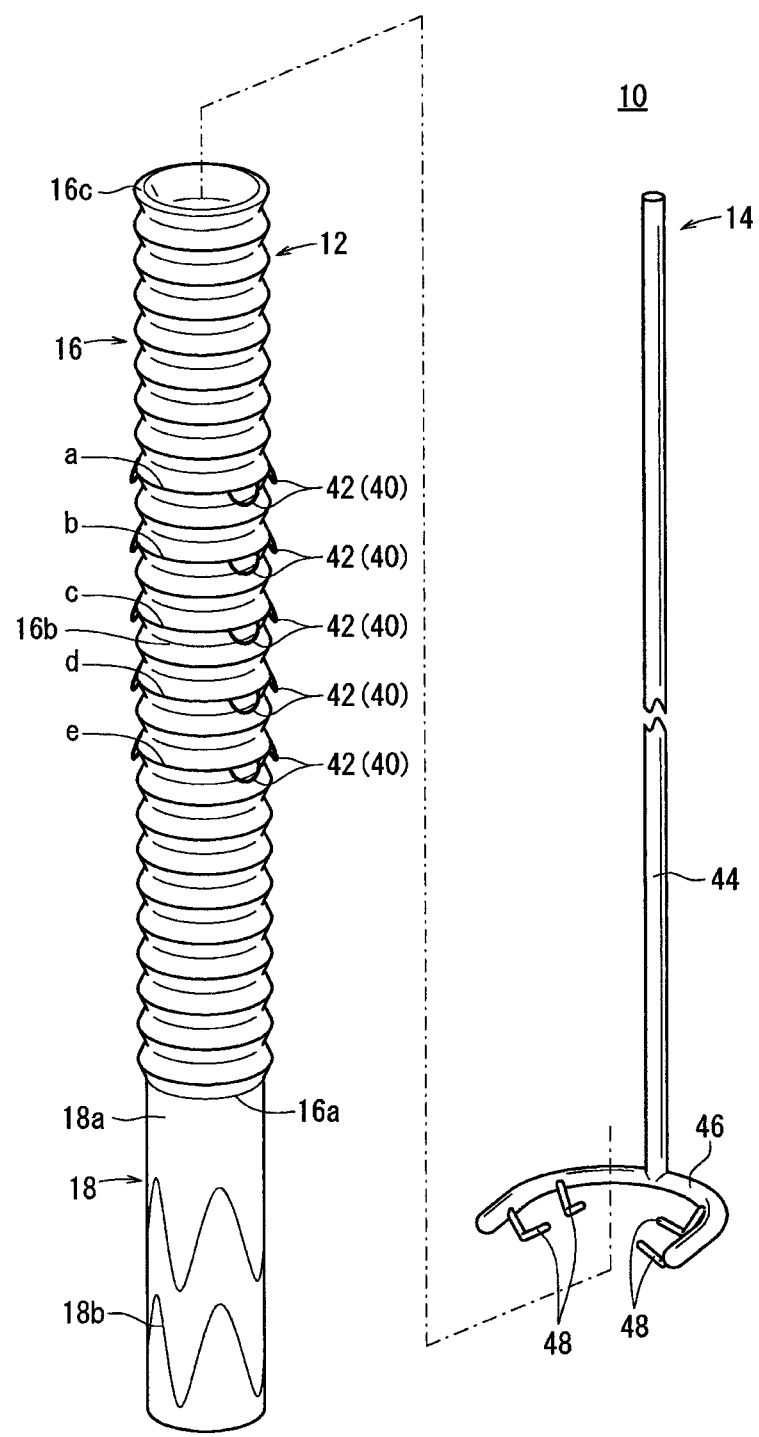
FIG. 2 is a perspective and exploded view of the overall configuration of the artificial blood vessel system.

FIGS. 1 and 2 illustrate an artificial blood vessel and artificial blood vessel system according to an embodiment disclosed here by way of example. The artificial blood vessel system 10 according to this embodiment includes an artificial blood vessel 12, and a position fixing device 14. As shown in FIG. 1, the artificial blood vessel 12 is used, for example, in a surgical therapy of an aortic arch 22 (aortic arch replacement surgery) as a substitute for the aortic arch 22 on a partial basis. The description below describes aortic arch replacement surgery as an example of the replacement surgery with which the artificial blood vessel disclosed here can be used, the artificial blood vessel 12 is not limited in this regard and may naturally be used as a replacement for other blood vessels.

As shown in FIGS. 1 and 2, the artificial blood vessel 12 has a tube 16 and a stent (structure) 18. The tube 16 of the artificial blood vessel 12 is formed from a material which is flexible and is applicable as a substitute for a living body blood vessel. Examples of the material which can be used here include artificial blank materials such as polyester fiber, ePTFE (expanded polytetrafluoroethylene), and polyurethane. In this case, the tube 16 may be formed by use of a hybrid blank material (hybrid artificial blood vessel) of which an inner peripheral surface is coated with a living body blank material such as endothelial cell, protein, etc. Furthermore, artificial blood vessels 12 formed by tissue engineering or gene engineering may also be applied or used.

The tube 16 is so sized and shaped as to be a relatively large-aperture artificial blood vessel for the region of chest that is suitable for replacement of the aortic arch 22. In this case, the tube 16 may have an outside diameter of about 12 to 30 mm, a material thickness of about 0.1 to 1 mm, and a length of about 100 to 600 mm, which is preferable in relation to, or when used as, the aortic arch 22.

For the tube 16 in this embodiment, a bellows structure is adopted so that its side surface does not collapse even when it is bent during a surgical operation. Instead of the bellows structure, the tube 16 may have a structure in which ring-shaped ribs are formed at the outer peripheral surface of the tube 16. Further, where the tube 16 itself has a certain degree of elasticity, the side surface of the tube 16 may be a smooth surface.

As shown in FIG. 2, the stent 18 is joined to one end portion 16a of the tube 16 mentioned above. The stent 18 is configured as a structure capable of being deformed to a first outside diameter which is a reduced diameter that is suitably sized for insertion into a blood vessel, and a second outside diameter which is greater than the first outside diameter and suitably sized for supporting the blood vessel from the inside. In addition, the stent 18 according to the present embodiment is configured as a stent graft in which a graft 18a formed from the same material as the tube 16 is combined with a metallic wire 18b. Examples of the material which can be used to form the wire 18b include medical stainless steel, Nitinol, tantalum, cobalt alloy, etc. A special wire capable of eluting a drug to be used to treat a diseased blood vessel can also be adopted.

The stent 18 has a structure in which the wire 18b formed from a metallic blank material having a restoring force such as a superelastic alloy possesses a wavy shape with respect to the circumferential direction of the graft 18a, and a plurality of (in FIG. 2, two) such wires 18b are arranged along the axial direction of the graft 18a. With this structure, the stent 18 functions as an elastic, self-expanding stent. The stent 18 may have an alternative structure such as one in which wires formed in a grid pattern or ring-like forms are attached to the graft 18a so as to expand the graft 18a in the circumferential direction. The stent 18 is not limited to the self-expanding stent as it is also possible to use a balloon-expandable stent in which a plastically deformable metallic blank material is formed into a meshed tube and which is expanded by dilating a balloon from the inside of the tube.

In the case of applying the artificial blood vessel 12 composed of the tube 16 and the stent 18 as above-mentioned to a living body blood vessel, the stent 18 is inserted into the lumen of a sheath tube (e.g., catheter) in a contracted state, specifically, in a state in which the stent 18 is deformed to the first or smaller outside diameter. Then, the artificial blood vessel 12 is inserted into the living body blood vessel together with the catheter, and thereafter the catheter is pulled out, whereby the stent 18 is allowed to expand (specifically, the stent 18 is allowed to deform to the second larger outside diameter). By the expansion of the stent 18, the graft 18a is pressed against the vessel wall of the living body blood vessel.

Referring to FIGS. 1-5, the description below discusses an example in which the artificial blood vessel 12 disclosed here is substituted for, or used in place of, an aortic arch 22. FIG. 5 schematically illustrates the vicinity of the aortic arch 22 before replacement with the artificial blood vessel 12. As shown in FIG. 5, the aortic arch 22 constitutes a part of a thoracic aorta 20 present near an upper portion of a heart, and permits the blood pumped out from the heart to flow therethrough.

In general, the thoracic aorta 20 includes an ascending aorta 24, the aortic arch 22, a descending aorta 26, a brachiocephalic trunk 28, a left common carotid artery 30 and a left subclavian artery 32. The ascending aorta 24 has a base portion 24a connected to an aortic ostium of the heart (left ventricle), and coronary arteries (right coronary artery 34a, left coronary artery 34b) for supplying oxygen to the cardiac muscles are connected to a lower portion of the ascending aorta 24. The aortic arch 22 is a part bent in an arched shape at an upper portion of the ascending aorta 24. The brachiocephalic trunk 28, the left common carotid artery 30 and the left subclavian artery 32 are branched from an upper portion of the aortic arch 22. The descending aorta 26 has an upper portion continuous with the aortic arch 22 and a lower portion continuous up to an abdominal aorta, and functions to supply the abdominal aorta with the blood pumped out from the heart.

In the case of replacing the aortic arch 22 with the artificial blood vessel 12 as a part of a surgical procedure, for example, a procedure may be adopted in which two parts in the ascending aorta 24 and the aortic arch 22 (or the descending aorta 26) are cut as indicated by cutting lines 100 and 102, and the brachiocephalic trunk 28, the left common carotid artery 30 and the left subclavian artery 32 branched from an upper portion of the aortic arch 22 are collectively cut along a cutting line 104.

As shown in FIG. 1, when the aortic arch 22 has been replaced with the artificial blood vessel 12 according to the present embodiment (in a situation in which the aortic arch replacement surgery has been performed), the stent 18 keeps its expanded state at a desired position (for example, in a site where the inside diameter of the blood vessel is comparatively small) in the descending aorta 26. This secures a state in which one end portion 16a of the tube 16 is fixed to the descending aorta 26. On the other hand, an intermediate portion 16b of the tube 16 is anastomosed with the trimmed end portion 22a of the aortic arch 22, whereby the aortic arch 22 and the descending aorta 26 are closed. Further, the intermediate portion 16b of the tube 16 exposed in the vicinity of the descending aorta 26 (i.e., a portion of the tube 16 outside the descending aorta 26) is cut out (notched) so that a cut-out portion remains in the intermediate portion 16b. A base portion 29 of the brachiocephalic trunk 28, the left common carotid artery 30 and the left subclavian artery 32 which have been cut collectively is anastomosed with this cut-out (notched) portion. In this condition, the other end portion 16c of the tube 16 and a base portion 24a of the ascending aorta 24 which has been cut are anastomosed with each other.

As above-mentioned, with the surgical system (frozen elephant trunk technique) in which the stent 18 provided as a part of the artificial blood vessel 12 is pressed against the inside of the descending aorta 26 and the artificial blood vessel 12 and the arteries are anastomosed with each other, the aortic arch 22 can be replaced with the artificial blood vessel 12, and blood is supplied from the heart to each of the arteries through the artificial blood vessel 12 after the replacement. This surgical system can offer great effects such as a reduction in the surgical invasiveness during treatment of aortic aneurysm or aortic dissection.

As described above, the aortic arch replacement surgery involves an end portion (the other end portion 16c) of the tube 16 where the stent 18 is not provided being folded back to the inside of the tube 16 (introversion), before the intermediate portion 16b of the tube 16 and the trimmed end portion 22a of the aortic arch 22 are anastomosed with each other (see FIG. 7). At the time when the folding-back work is conducted, the artificial blood vessel 12 is locked in the vicinity of the trimmed end portion 22a of the aortic arch 22, whereby the artificial blood vessel 12 is prevented from being pushed into the aortic arch 22 or the descending aorta 26 by the pushing-in force attendant on the folding-back work.

Figure 3A:
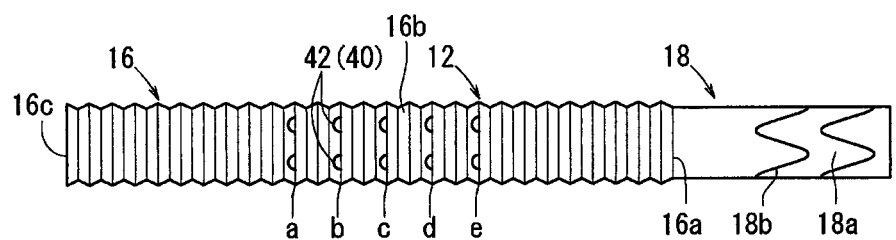

The artificial blood vessel system 10 according to this embodiment disclosed by way of example includes the position fixing device 14 as a configuration for locking the tube 16. As shown in FIG. 2 and FIG. 3A, the artificial blood vessel 12 according to the present embodiment has a plurality of lock parts 40 at the intermediate portion 16b of the tube 16. The lock parts 40 are locked by the position fixing device 14.

By way of example, the lock part 40 can be a thread-like hooking part (arcuate hooking part) 42 having both end portions fixed to the outer peripheral surface of the tube 16. With the hooking parts 42 thus applied as the lock parts 40, the hooking parts 42 can be relatively easily attached to the outer peripheral surface of the tube 16.

In addition, in the present embodiment, four such hooking parts 42 are arranged in the circumferential direction (i.e., four hooking parts are provided on one ridgeline of the bellows structure) of the tube 16. The four hooking parts 42 are positioned so that one pair of hooking parts 42 is arranged at a certain interval (for example an angular interval of 30 degrees between the two hooking parts forming the pair) at a side portion on one side of the tube 16, and in symmetry with this, another pair of the hooking parts 42 is similarly arranged at a certain interval (for example an angular interval of 30 degrees between the two hook parts forming the pair) at a side portion on the other side (opposite side) of the tube 16. It is also possible for the four hooking parts 42 to be arranged at regular angular intervals of 90 degrees.

In this illustrated embodiment disclosed by way of example, five rows of hooking parts 42 are present on the outer peripheral surface of the tube 16, with each row being composed of four hooking parts 42 arranged along the circumferential direction. The five rows of hooking parts 42 are axially arranged along the axial direction of the tube 16 (the rows are denoted by symbols a to e sequentially from the upper side in FIG. 2, and each row will hereafter be referred to also as "lock row"). The intervals between the lock rows a to e are set to be regular intervals (i.e., the same interval or distance) when the tube 16 extends in a straight line form.

The position fixing device 14 of the artificial blood vessel system 10 operates to lock the hooking parts 42 (lock parts 40) of the tube 16 described above. The hooking parts 42 of the tube 16 are thus fixed in place by the position fixing device 14. The position fixing device 14 is composed of a bar section 44 extending in a straight line form, and a U-shaped section 46 bifurcated from an end portion of the bar section 44 so as to have a substantially arcuate shape. The two sections 44 and 46 being integrally molded from a resin material exhibiting elasticity. The U-shaped section 46 projects in a direction orthogonal to the extending direction of the bar section 44. The position fixing device 14 is so configured that when the bar section 44 is matched to, or positioned generally parallel to, the extending direction of the tube 16, the U-shaped section 46 partly surrounds the side portion of the tube 16.

Figure 3B:
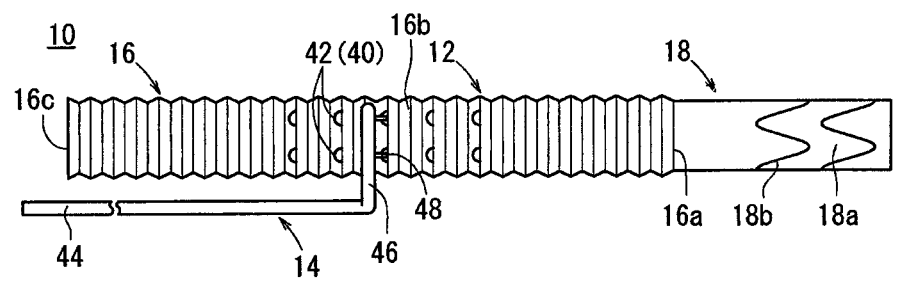
Figure 3C:
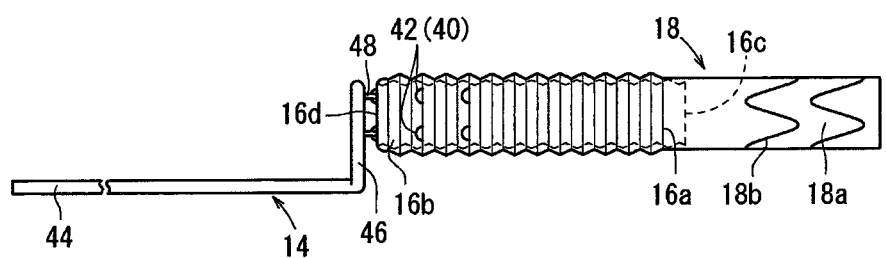

The U-shaped section 46 has hooks (hook sections) 48 for engaging or hooking the hooking parts 42 of the tube 16. Each of the hooks 48 is arranged at a position corresponding to each of the hooking parts 42 disposed in the hook rows a to e, and projects toward the inside diameter side of the U-shaped section 46. Each of the hooks 48 is hooked on one hooking part 42 in the desired hook row a to e when the tube 16 is locked by the position fixing device 14 as shown in FIG. 3B. Thus, the four hooking parts 42 provided along the circumferential direction of the tube 16 are hooked respectively on the four hooks 48 of the position fixing device 14, whereby the position fixing device 14 can relatively reliably lock the tube 16, and the tube 16 can be rather easily folded back from the other end portion 16c to the inside as seen in FIG. 3C. Consequently, in the artificial blood vessel 12, the tube 16 is assuredly fixed at the lock position, even if a strong pushing-in force is exerted thereon during the work of folding back the tube 16.

In addition, with the plurality of lock rows a to e provided along the axial direction of the tube 16, the position of locking of the tube 16 by the position fixing device 14 can be changed in a selective manner. This makes it possible for the fold-back amount of the tube 16 to be freely set according to, for example, the size of the descending aorta 26 or the region of therapy, or other factors.

Accordingly, by a process in which the folded end portion 16d formed by folding back the tube 16 is reliably positioned in the vicinity of the trimmed end portion 22a of the aortic arch 22, it is possible to further facilitate the work of anastomosing the folded end portion 16d with the trimmed end portion 22a of the aortic arch 22.

Furthermore, the U-shaped section 46 of the position fixing device 14 according to the present embodiment has elasticity, and is so configured that in the state in which the hooking parts 42 are locked by the hooks 48, each of the hooking parts 42 is pulled toward the outside diameter side. When the hooking parts 42 arranged in the circumferential direction of the tube 16 are pulled toward the outside diameter side, the tube 16 at that position can be enlarged in inside diameter, and, when the other end portion 16c of the tube 16 is folded back in this state, the folded end portion 16d can be formed in a desired shape. This makes it possible to facilitate the anastomosis between the folded end portion 16d and the trimmed end portion 22a of the aortic arch 22, and to perform the surgery for replacement with the artificial blood vessel more efficiently.

When the replacement with the artificial blood vessel 12 has been done, the hooking parts 42 are left on the outer peripheral surface of the tube 16. Because the hooking parts 16 protrude by only a relatively tiny amount relative to the anastomosis thread (suture) for anastomosis between the artificial blood vessel 12 and the living body blood vessel, the hooking parts 42 are not liable to produce bad influences on the human body. Alternatively, a configuration may be adopted in which the hooking parts 42 are detachable from the tube 16 and the removal of the hooking parts 42 is conducted after the anastomosis between the folded end portion 16d of the tube 16 and the trimmed end portion 22a of the aortic arch 22.

In addition, the anastomosis thread used for anastomosis between the artificial blood vessel 12 and the living body blood vessel can be used as the hooking parts 42. In this case, the thread is preferably made from a material which is decomposed in the living body and is not harmful to the human body. Examples of the applicable material include biodegradable polymers such as gelatin, fibrin, cellulose, etc., and such inorganic materials as phosphoric acid compounds, carbonic acid compounds, etc. With the hooking parts 42 formed from such a material, the hooking parts 42 can be decomposed in the living body after the replacement with the artificial blood vessel 12.

Set forth below with reference to FIGS. 4-9 is a discussion of the aortic arch replacement surgery procedure using the artificial blood vessel system 10 according to the present embodiment disclosed here by way of example. In the aortic arch replacement surgery, a thoracic incision is applied to the region of chest of the patient, the aortic arch 22 or the descending aorta 26 is trimmed, and the artery to be replaced with the artificial blood vessel 12 is removed (step S1 in FIG. 4). As the thoracic incision, normally a thoracic midline incision is performed for the purpose of lessening the operative invasion to the patient. However, a left thoracic incision may be performed according to the conditions of disease or the like. At the time of dissecting/trimming the aortic arch 22, extracorporeal circulation of blood may be carried out using a heart-lung machine or the like, as required. Then, as shown in FIG. 5, the thoracic aorta 20 is cut along cutting lines 100, 102 and 104 at three positions, and the aortic arch 22 is cut off from the arteries of the thoracic aorta 20.

Thereafter, the artificial blood vessel 12 with the associated stent 18 loaded in a catheter is inserted into the descending aorta 26, and the artificial blood vessel 12 (stent 18) is fed into a predetermined indwelling position in the descending aorta 26, for example into the site where the descending aorta 26 is narrowed in outside diameter in FIG. 6) (step S2 in FIG. 4). In this case, the stent 18 of the artificial blood vessel 12 is contained in the catheter with the stent 18 in its first-outside-diameter state (i.e., smaller outside diameter state).

Next, the stent 18 at the indwelling position is expanded from the first outside diameter to the larger second outside diameter, thereby pressing the artificial blood vessel 12 against the vessel wall of the descending aorta 26 (step S3 in FIG. 4). To do this, the catheter is pulled off from the stent 18 inserted to the desired position in the descending aorta 26, whereby the stent 18 is permitted to expand automatically. Consequently, the stent 18 is pressed against the descending aorta 26, as shown in FIG. 6. As a result of the above-mentioned work, a state is established in which the other end portion 16c of the artificial blood vessel 12 extends to a base portion 24a of the ascending aorta 24, and the intermediate portion 16b of the artificial blood vessel 12 is exposed to the exterior of the arteries after passing through an upper portion and the trimmed end portion 22a of the descending aorta 26.

Subsequently, the hooks 48 of the position fixing device 14 are engaged with the hooking parts 42 of the tube 16, and the tube 16 is thereby locked (step S4 in FIG. 4). In this case, one of the lock rows a to e (for example, in FIG. 6, the lock row c located closest to the trimmed end portion 22a of the aortic arch 22) is selected according to the location of the trimmed end portion 22a of the aortic arch 22, and the four hooks 48 of the position fixing device 14 are hooked on the four hooking parts 42 provided in the lock row c.

Then, in the state in which the lock row c is positioned and held by the position fixing device 14, the other end portion 16c of the tube 16 is folded back to the inside using forceps or the like, whereby the folded end portion 16d is eventually formed at such a position as to substantially overlap with the trimmed end portion 22a of the aortic arch 22 (at the position where the lock row c is locked by the position fixing device 14), as shown in FIG. 7 (step S5 in FIG. 4).

Subsequently, the folded end portion 16d of the tube 16 and the trimmed end portion 22a of the aortic arch 22 are anastomosed with each other (step S6 in FIG. 4). In this instance, as above-mentioned, the folded end portion 16d of the tube 16 is formed at such a position as to substantially overlap with the trimmed end portion 22a of the aortic arch 22, whereby the anastomosis can be carried out relatively easily and accurately (see FIG. 8). By virtue of the anastomosis, the trimmed end portion 22a of the aortic arch 22 is closed. Thus, according to the method of joining the artificial blood vessel 12 in which steps S1 to S6 are carried out, the folding back operation of the artificial blood vessel 12 can be carried out in a relatively short time. In addition, the tube 16 can be folded back cleanly (in a desired shape), whereby the artificial blood vessel 12 can be joined to the living body blood vessel (aortic arch 22) more easily. Consequently, the total working efficiency of the surgical operation can be enhanced.

After the anastomosis is finished, the other end portion 16c of the tube 16 thus folded is returned into its original state (step S7 in FIG. 4). In this case, since the tube 16 has been locked while folding back the tube 16 in step S5, the tube 16 has been folded back relatively cleanly and so the other end portion 16c of the tube 16 can be efficiently returned into its original state.

Next, the upper side of the intermediate portion 16b of the tube 16 is cut (step S8 in FIG. 4). Specifically, as shown in FIG. 9, that part of the tube 16 which is exposed from the descending aorta 26 is cut along a cutting line 106, whereby a cutout region (notch) exists at an upper part of the intermediate portion 16b of the tube 16.

Finally, the ascending aorta 24 is anastomosed with the other end portion 16c of the tube 16, and a base section 29 of the arteries (the brachiocephalic trunk 28, the left common carotid artery 30, the left subclavian artery 32) is anastomosed with the cutout region of the intermediate portion 16b of the tube 16 having been cut (step S9 in FIG. 4). As a result, the artificial blood vessel 12 is joined to the arteries, and a state in which the aortic arch 22 is replaced with the artificial blood vessel 12 is completed, as shown in FIG. 1.

As above-described, according to the artificial blood vessel system 10 of the present embodiment, the tube 16 of the artificial blood vessel 12 is positioned and held at a desired position by the position fixing device 14, whereby the tube 16 can be relatively easily folded back to the inside (to the inside of the tube 16 itself). Therefore, the other end portion 16c of the tube 16 can be folded back to the vicinity of the trimmed end portion 22a in a fairly short time. This helps ensure that the surgical operation for replacement with the artificial blood vessel 12 can be carried out more efficiently, and that the burden on the patient is reduced or alleviated.

While the lock parts 40 of the tube 16 are locked by use of the position fixing device 14 in this embodiment, the lock parts 40 may be locked by forceps or the like according to the size of the operative region, the region of therapy, or the like. In the artificial blood vessel system 10, the locking of the tube 16 may also be accomplished by use of a position fixing device which has a suction function for holding the outer peripheral surface of the tube 16 by suction.

In this disclosed and illustrated embodiment, the hooks 48 of the position fixing device 14 are hooked on the hooking parts 42 of the tube 16 in step S4 of the aortic arch replacement surgery. This configuration, however, is not limitative. For example, a configuration may be adopted in which the hooks 48 of the position fixing device 14 are preliminarily hooked on the hooking parts 42 of the tube 16 before step S2, according to the size of the operative region, the region of therapy or the like, then the artificial blood vessel 12 in this state is inserted into the descending aorta 26 (step S2), and, thereafter, the position fixing device 14 caught on the artificial blood vessel 12 is pulled out of the descending aorta 26, thereby locking the tube 16 (step S4).

In short, it is sufficient in the artificial blood vessel system 10 to cause the tube 16 to be locked at a desired position at the time of performing the work of folding back the tube 16, and the configuration, shape, function, timing of locking, etc. of the position fixing device 14 for the locking are not specifically restricted.

FIGS. 10A and 10B illustrate an artificial blood vessel 50 according to a first modification. In the description below of this first modification, as well as the subsequent descriptions of the second and third modifications, aspects of the first to third modifications that are the same as in the artificial blood vessel system 10 described above are denoted by the same reference symbols, and a detailed description of such features and aspects of the artificial blood vessel and artificial blood vessel system is not repeated.

As shown in FIGS. 10A and 10B, the artificial blood vessel 50 according to the first modification differs from the artificial blood vessel 12 described above in that two artificial blood vessels (a first artificial blood vessel 52 and a second artificial blood vessel 54) are used. In this case, the first artificial blood vessel 52 has a tube 16 and a stent 18, like the artificial blood vessel 12 described above. On the other hand, the second artificial blood vessel 54 includes a main blood vessel 56 of the same size as the tube 16 of the first artificial blood vessel 52, and three branch blood vessels 56a, 56b, 56c which are connected to the main blood vessel 56 and which can replace base portions of the arteries (the brachiocephalic trunk 28, the left common carotid artery 30 and the left subclavian artery 32) near an upper portion of the aortic arch 22. The artificial blood vessel 50, in which one end portion 54a of the second artificial blood vessel 54 is integrally anastomosed with the other end portion 16c of the first artificial blood vessel 52, is substituted for a living blood vessel (the aortic arch 22) requiring therapy or treatment.

In addition, the tube 16 forming the first artificial blood vessel 52 is shorter than the artificial blood vessel 12 according to the above embodiment. As a result, in a state in which the first artificial blood vessel 52 is inserted in the aortic arch 22, the tube 16 (the other end portion 16c) protrudes a little from the anastomosed part. Therefore, with lock parts 40 (hooking parts 42) provided on the outer peripheral surface of the tube 16 of the first artificial blood vessel 52, the lock parts 40 can be fairly easily positioned and held by use of a position fixing device 14 or the like.

A method of joining the artificial blood vessel 50 according to the first modification is now described. First, a thoracic incision is applied to the region of chest of the patient, the aortic arch 22 is trimmed, and the arteries to be replaced with the artificial blood vessel 50 are removed (step S1 in FIG. 4). In this instance, as shown in FIG. 10A, the thoracic aorta 20 is trimmed along a cutting line 110 on the ascending aorta 24 side, a cutting line 112 on the aortic arch 22 side, and cutting lines 114a, 114b and 114c near the base portions of the brachiocephalic trunk 28, the left common carotid artery 30 and the left subclavian artery 32.

After the removal of the arteries, the procedure for joining the first artificial blood vessel 52 to the aortic arch 22 can be carried out by adopting steps similar to steps S2-S7 in FIG. 4 described in the method of joining the artificial blood vessel 12 in the above embodiment. After step S7 is finished and the tube 16 of the first artificial blood vessel 52 is returned from the folded state to the original state, the other end portion 54b of the second artificial blood vessel 54 is anastomosed with the ascending aorta 24. Furthermore, the three branch blood vessels 56a, 56b and 56c are anastomosed respectively with the relevant arteries (the brachiocephalic trunk 28, the left common carotid artery 30 and the left subclavian artery 32), followed by anastomosing the first artificial blood vessel 52 with the second artificial blood vessel 54.

Thus, according to the first modification, the tube 16 is positioned and held by the position fixing device 14 or the like at the time of folding back the other end portion 16c of the first artificial blood vessel 52 to the inside, whereby the other end portion 16c of the tube 16 can be folded back up to the trimmed end portion 22a in a fairly short time so that the burden on the patient can be alleviated. In addition, the combination of the first artificial blood vessel 52 and the second artificial blood vessel 54 makes it possible to perform a replacement surgery with high versatility according to the region of therapy or treatment of the living body blood vessel (for example, the case where a disease exists in the vicinity of an upper-side portion of the aortic arch 22). The first artificial blood vessel 52 may be an artificial blood vessel obtained by cutting short the artificial blood vessel 12 according to the above embodiment. And the artificial blood vessel 50 may be one in which the first artificial blood vessel 52 and the second artificial blood vessel 54 are preliminarily united together.

FIGS. 11A and 11B are illustrations of a method of joining an artificial blood vessel according to a second modification disclosed here. As shown in FIGS. 11A and 11B, in the second modification, the artificial blood vessel 12 according to the above embodiment can be used, and the second modification differs from the above embodiment in only the method of joining the living body blood vessel and the artificial blood vessel 12 described in the above embodiment. Specifically, in the second modification, a joining method is adopted in which the artery (the aortic arch 22 or the ascending aorta 24) on the upstream side is inserted into the other end portion 16c of the artificial blood vessel 12, and an outer peripheral surface (side surface) of the artery on the upstream side and a part near the other end portion 16c of the artificial blood vessel 12 are anastomosed with each other.

In this case, as shown in FIG. 11A, the thoracic aorta 20 is trimmed along a cutting line 120 in the aortic arch 22 near the ascending aorta 24, a cutting line 122 in the aortic arch 22 near the descending aorta 26, and a cutting line 124 on the side of a base portion 29 of the brachiocephalic trunk 28, the left common carotid artery 30 and the left subclavian artery 32. In the second modification, dissection or trimming is performed in such a manner that the cutting line 122 is continuous with the cutting line 124.

In the second modification, at the time of executing step S9 after the steps (steps S2 to S8 in FIG. 4) described above with respect to the method of joining the artificial blood vessel 12 in the above embodiment, the operation of anastomosing the intermediate portion 16b of the tube 16 with the base portion 29 and the operation in which the aortic arch 22 cut at the cutting lines 120 and 124 is inserted into the tube 16 (the other end portion 16c) of the artificial blood vessel 12 and the overlapping parts of the tube 16 and the aortic arch 22 are anastomosed with each other are performed. Thus, the artery on the upstream side is inserted into the inside of the artificial blood vessel 12 and anastomosis is conducted in this state, whereby the artificial blood vessel 12 can be easily put into firm contact with the living body blood vessel.

Also in the second modification, the tube 16 is positioned and held by use of a position fixing device 14 or the like at the time of folding back the other end portion 16c of the artificial blood vessel 12 to the inside. This makes it possible to fold back the other end portion 16c of the tube 16 up to the vicinity of the trimmed end portion 22a in a fairly short time, and to lighten the burden on the patient.

FIGS. 12A and 12B are illustrations of a method of joining an artificial blood vessel according to a third modification disclosed here. As shown in FIGS. 12A and 12B, the artificial blood vessel 60 according to the third modification differs from the artificial blood vessel 12 described in the above embodiment in that the tube 16 is cut short according to the region of therapy (replacement site) of the aortic arch 22.

Specifically, as shown in FIG. 12A, the thoracic aorta 20 is trimmed along a cutting line 130 between the left subclavian artery 32 and the left common carotid artery 30 of the aortic arch 22, a cutting line 132 in the aortic arch 22 near the descending aorta 26, and a cutting line 134 at a base portion of the left subclavian artery 32. By use of the artificial blood vessel 60 according to the third modification, the end portion of the aortic arch 22 cut at the cutting line 130 and the other end portion 16c of the artificial blood vessel 60 are anastomosed with each other, and, further, the left subclavian artery 32 is anastomosed with an upper part of the other end portion 16c, whereby the living body blood vessel can be replaced with the artificial blood vessel 60.

Where the third modification is adopted, the region of replacement of the thoracic aorta 20 can be minimized, so that the burden on the patient can be further alleviated. In addition, with the lock parts 40 (hooking parts 42) provided on the outer peripheral surface of the tube 16 of the artificial blood vessel 60, the lock parts 40 can be relatively easily positioned and held by use of a position fixing device 14 or the like. Consequently, the other end portion 16c of the tube 16 can be folded back up to the vicinity of the trimmed end portion 22a in a short time.

The detailed description above describes features and aspects of embodiments of an artificial blood vessel, artificial blood vessel system, and method of performing replacement surgery using an artificial blood vessel. The invention is not limited, however, to the precise embodiments and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. An artificial blood vessel configured to replace a portion of a blood vessel in a living body which has been removed from a remaining portion of the blood vessel in the living body, the artificial blood vessel comprising:

a flexible tube having a continuous outer peripheral surface and a portion configured to be fixed to a first part of the remaining portion of the blood vessel in the living body, the flexible tube possessing an inside, one end portion and an oppositely located other end portion, a structure fixed to the one end portion of the tube and configured to be positioned inside a second part of the remaining portion of the blood vessel in the living body, the structure being deformable between a first outside diameter and a second outside diameter, with the second outside diameter being greater than the first outside diameter; and the tube including a lock part fixed to the outer peripheral surface of the tube such that the lock part projects outwardly from the outer peripheral surface, the lock part being configured to be locked at a desired position by a position fixing device when the other end portion of the tube is folded back to the inside of the tube.

2. The artificial blood vessel according to claim 1, wherein a plurality of the lock parts are fixed to the outer peripheral surface of the tube at axially spaced apart positions.

3. The artificial blood vessel according to claim 1, wherein the tube includes a plurality of the lock parts, and wherein the tube is bellows-shaped so that an outer periphery of the tube possesses a plurality of circumferentially extending and axially spaced apart ridgelines, the plurality of lock parts being circumferentially spaced apart on one of the ridgelines.

4. The artificial blood vessel according to claim 1, wherein the lock part is an arcuate hooking part having opposite ends which are both fixed to the outer peripheral surface of the tube.

5. The artificial blood vessel according to claim 1, wherein a plurality of the lock parts are fixed to the outer peripheral surface of the tube, the plurality of lock parts being arranged in axially spaced apart rows, each row of lock parts comprising a plurality of circumferentially spaced apart lock parts.

6. An artificial blood vessel system for replacing a portion of a blood vessel in the living body which has been removed from a remaining portion of the blood vessel, the artificial blood vessel system comprising:

a flexible tube having a continuous outer peripheral surface and a portion configured to be fixed to a first part of the remaining portion of the blood vessel in the living body, the flexible tube possessing an inside, one end portion and an oppositely located other end portion, a structure fixed to the one end portion of the tube and configured to be positioned inside a second part of the remaining portion of the blood vessel in the living body, the structure being deformable between a first outside diameter and a second outside diameter, with the second outside diameter being greater than the first outside diameter;

a lock part fixed to the outer peripheral surface of the tube such that the lock part projects outwardly from the outer peripheral surface; and a position fixing device for positioning and holding the tube at a desired position when the tube is folded back from its other end portion to the inside, the position fixing device including a hook section configured to engage the lock part.

7. The artificial blood vessel system according to claim 6, wherein a plurality of axially spaced apart lock parts are fixed to the outer peripheral surface of the tube, and the hook section is configured to permit a change in a position at which the tube is held by the position fixing device along an axial direction of the tube when the tube is folded back from its other end portion to the inside by selectively engaging the hook section with lock parts having different axial positions.

8. The artificial blood vessel system according to claim 6, wherein the tube includes a plurality of the lock parts, and wherein the tube is bellows-shaped so that an outer periphery of the tube possesses a plurality of circumferentially extending and axially spaced apart ridgelines, the plurality of lock parts being circumferentially spaced apart on one of the ridgelines, and the position fixing device has a plurality of hook sections corresponding to the lock parts and locks the lock parts by the hook sections.

9. The artificial blood vessel system according to claim 8, wherein the position fixing device is configured to pull the lock parts outwardly when the lock parts are locked by the hook sections.

10. The artificial blood vessel system according to claim 6, wherein the lock part is an arcuate hooking part having opposite ends which are both fixed to the outer peripheral surface of the tube, and the hook section projects inwardly from the inside of a U-shaped section of the position fixing device which is configured to accept the tube.

11. An artificial blood vessel configured to replace a portion of a blood vessel in a living body which has been removed from a remaining portion of the blood vessel in the living body, the artificial blood vessel comprising:

a flexible tube having a continuous outer peripheral surface and a portion configured to be fixed to a first part of the remaining portion of the blood vessel in the living body, the flexible tube possessing an inside, one end portion and an oppositely located other end portion, a structure fixed to the one end portion of the tube and configured to be positioned inside a second part of the remaining portion of the blood vessel in the living body, the structure being deformable between a first outside diameter and a second outside diameter, with the second outside diameter being greater than the first outside diameter; and the tube including a hooking part fixed to the outer peripheral surface of the tube between the one end portion and the other end portion such that the hooking part projects outwardly from the outer peripheral surface, the hooking part being configured to be locked at a desired position by hooking engagement with a position fixing device when the other end portion of the tube is folded back to the inside of the tube, the hooking part comprising a thread.

* * * * *